United States Patent [19]

Ilies

[11] 4,405,602

[45] Sep. 20, 1983

[54] PROCESS FOR THE OBTAINMENT OF A BIOLOGICALLY ACTIVE BEE-PRODUCT

[75] Inventor: Nicoláe Ilies, Bucharest, Romania

[73] Assignee: Cooperativa Agricola de Productie Scornicesti, Judetul Olt, Romania

[21] Appl. No.: 305,629

[22] PCT Filed: Jan. 21, 1981

[86] PCT No.: PCT/RO81/00001

§ 371 Date: Sep. 16, 1981

§ 102(e) Date: Sep. 16, 1981

[87] PCT Pub. No.: WO81/02106

PCT Pub. Date: Aug. 6, 1981

[30] Foreign Application Priority Data

Jan. 21, 1980 [RO] Romania .................................. 999/21

[51] Int. Cl.³ ...................... A61K 35/64; A61K 47/00; A23L 1/34

[52] U.S. Cl. ...................................... 424/95; 424/358; 426/641

[58] Field of Search ................... 424/95, 358; 426/641

[56] References Cited

FOREIGN PATENT DOCUMENTS 1503586 10/1967 France .

OTHER PUBLICATIONS

Bordas–Chem. Abst. vol. 69, (1968), p. 109, 757c.

*Primary Examiner*—Sam Rosen
*Attorney, Agent, or Firm*—Karl F. Ross; Herbert Dubno

[57] ABSTRACT

A new process is disclosed for the preparation of a biologically active bee product under sterile conditions. In the process drone bee larvae, worker bee larvae or queen bee larvae are picked up before respective cell capping together with larval food contained in comb cells to form a mixture of crude larval triturate. The mixture is then triturated and filtered to remove impurities to yield the desired product. The product is useful as an animal feed and in the preparation of royal jelly.

8 Claims, No Drawings

PROCESS FOR THE OBTAINMENT OF A BIOLOGICALLY ACTIVE BEE-PRODUCT

TECHNICAL FIELD

The present invention relates to a process for the preparation of a biologically active bee-product meant as food, containing vitalizing and regenerating substances, mainly amino-acids, hormones, vitamins and mineral salts. Use can also be made of the said process as described by the invention in order to obtain a bee-product employed as a most biologically active raw material in the apitherapeutic and cosmetic industry.

PRIOR ART

It is known that the food the nurse bees give to the three categories of individuals: queen bee, worker bee and drone, during the first days of their embryonic development, is of identical quality and is known as royal jelly which is a purely glandular secretion greatly influencing their entire later metamorphosis in the larval and pupal stages.

After a first three-day long post-embryonic stage the worker and drone larvae are offered a kind of food which is qualitativety different from the royal jelly, consisting of a nutritive mixture made of pollen, bee bread, honey and water (the worker develops from a fertilized egg and the drone from a non-fertilized one).

The larval stage of the drone lasts for 8 days, i.e. the eleventh day since the egg has been laid, when the cell is capped, the larva ceases to be fed from outside and the pupal stage starts and lasts for 11–12 days.

The differentiated feeding of the drone larvae in the larval stage leads, by the contribution of pollen, bee-bread and honey to an increase in the sugars and protein nutritive value of the substances contained in the cells of the drone larvae (Barac I et al. "Beebreeding", Editura Agrosilvica, Bucharest 1965 )

Research works concerning the determination of the chemical composition of bee larvae are also known (Dewey M. Caron, American Bee Journal, 1978, 389).

SUMMARY OF THE INVENTION

Taking into account the composition of the drone larvae, very rich in nutritive substances, the present invention aims at obtaining a biologically active product summing up all the nutritive substances contained in the body of the drone larvae and in the larval food contained in the comb cells from which the larvae are picked up.

Consequently, the said process, as described by the invention, provides for the trituration of the drone larvae picked up in the 10-th day since the non-fertilized egg has been laid, together with the whole content of the respective comb cells, homogenization and filtration of the triturate resulting in a "fresh product" and, when needed, the lyophilization of the mixture resulting in a "standard dehydrated product". Picking up, trituration and filtration are to be made under sterile conditions.

The fresh product, obtained as stated above, will be kept at temperatures ranging between $-5°$ to $-15°$ C.

This process can also be applied to queen bee larvae or to worker larvae, by modifying the date when larvae are picked up depending on the duration of individual metamorphosis e.g., a day before cell capping.

The physical and chemical characteristics of the larval triturate prior to lyophilisation are the following:

Aspect: viscous and homogeneousmass with a fine granulation
Colour: white with a tendency of greyish-brownish shading
Consistency: milky, unctuous, slightly viscous
Smell: characteristic of larval food, slightly flavoured
Taste: cream-like, slightly astringent without disagreeable sensations.
Impurities:
upon macroscopic analysis:
pieces of wax, untriturated larvae, epithelia, Varoa mites or any matters of a nature other than that of the product as described by the invention are not admitted.
upon microscopic analysis:
pieces of larvae or epithelia are not admitted. Isolated larval cells, pollen cells (maximum 1–30/microscopic field), yeasts (maximum 25/microscopic field) are admitted.

| | |
|---|---|
| pH | 4.8–6.7 |
| moisture content % | 65–80 |
| dry matters content g % | 20–35 |
| proteins, total g % | 10–20 |
| sugars, total g % | 1.00–5.50 |
| lipids, total g % | 5.00–6.30 |
| ash g % | 1.00–1.50 |
| indeterminate matters g % | 4.00–6.00 |
| minimum diastase number g % | 20.0–29.5 |
| density | 1.1–1.2 |
| free aminoacids g % | 1.0–1.3 |
| glucidic structure the product: | |
| glucose | 3.16%–5% |
| fructose | 0.03%–0.5% |
| saccharose | 0.03%–0.5% |

| Mineral salts | | |
|---|---|---|
| calcium | mg % | 14.00 |
| magnesium | mg % | 2.00 |
| phosphorus | mg % | 190.00 |
| iron | mg % | 3.23 |
| copper | mg % | 1.10 |
| manganese | mg % | 4.49 |
| zinc | mg % | 5.54 |
| sodium | mg % | 38.00 |
| potassium | mg % | 0.50 |

| Vitamins | | |
|---|---|---|
| Vitamin A | | 0.54 UI/g |
| betacarotene (provitamin A) | mg % | 0.426 |
| xantophile | mg % | 0.297 |
| Vitamin $B_1$ | | under the dose limit |
| Vitamin $B_2$ | g % | 0.739 (739 gamma %) |
| Vitamin PP (nicotinic acid) | mg % | 15.8 |
| Cholin | mg % | 442.8 |

| Amino-acids | |
|---|---|
| lysine | 0.75 g %, |
| histidine | 0.33 g % |
| arginine | 0.51 g % |
| aspartic acid | 1.5 g % |
| threonine | 0.41 g % |
| serine | 0.46 g % |

| Amino-acids | |
|---|---|
| glutamic acid | 1.73 g % |
| proline | 0.8 g % |
| glycine | 0.84 g % |
| alanine | 0.66 g % |
| valine | 0.68 g % |
| methionine | 0.31 g % |
| isoleucine | 0.56 g % |
| leucine | 0.95 g % |
| tyrosine | 0.45 g % |
| phenylalanine | 0.46 g % |
| cystine | none |
| (Total 11.4 g % amino-acids) | |

The product also contains hormone-like compounds, originating in the larval sexual structures, already developed the day the larvae are picked up.

Applicability of invention

The process, as described by the invention, makes possible the preparation of a natural biologically active product which can be used in human nourishment as such or in a 1–3% honey mixture or in combination with several other bee-products (pollen, propolis etc) or with natural products such as extracts from aromatic plants.

It also makes possible the preparation of a product to be used in apiculture by adding it in a 2–3 g ratio to one liter of stimulative syrup given to royal jelly producing colonies, resulting in a significant increase of the royal jelly yield per colony.

The process also enables the obtainment of a natural nutritive and bioregenerating product for the epidermis, usable in the cosmetic industry for nourishing beauty creams, lotions, sprays, etc.

In the industrial intensive poultry breeding system, the product obtained according to this invention can be used in fodder premixes, completing the mix-fodder recipes. For the corresponding development of 0–30 days old chicken the quality of food improved by using the product obtained according to the invention has a major role for the whole period of later development.

The process, as described by the invention, is highly valuable upon the enrichment of the range of aphitherapeutic products.

I claim:

1. A process for the preparation of a biologically active bee product under sterile conditions which comprises the steps of:
   (a) picking up drone bee larvae, worker bee larvae or queen bee larvae before respective cell capping together with larval food contained in comb cells to form a mixture of crude larval triturate;
   (b) triturating the mixture formed during step (a); and
   (c) filtering the mixture triturated during step (b) to obtain the desired fresh product.

2. The process defined in claim 1 further comprising the step of:
   (d) dehydrating-lyophilizing the product formed during step (c) in order to obtain a standard dehydrated product.

3. The process defined in claim 1 wherein the dehydrated product obtained during steps (a), (b) and (c) is stored at a temperature of $-5°$ to $-15°$ C.

4. The process defined in claim 1, step (a), wherein the drone bee larvae are picked up on the tenth day after the nonfertilized egg has been laid.

5. The process defined in claim 1, step (a), wherein worker bee larvae or queen bee larvae are picked up one day before respective cell capping.

6. The product obtained by the process defined in claim 1.

7. A method of feeding poultry which comprises the steps of:
   (a) adding the product prepared by the process defined in claim 1 to a fodder premix; and
   (b) feeding the product to the poultry.

8. A method of increasing royal jelly production in a bee colony which comprises the steps of:
   (a) adding the product produced by the process defined in claim 1 in a 2 to 3 g ratio to 1 liter of stimulating syrup given to royal jelly-producing bee colonies; and
   (b) feeding the stimulating syrup enriched by adding the product defined in claim 3 to a royal jelly-producing bee colony.

* * * * *